United States Patent [19]

Carmosin et al.

[11] Patent Number: 4,683,239
[45] Date of Patent: Jul. 28, 1987

[54] 3-DIPHENYL SUBSTITUTED OCTAHYDROINDOLIZINE ANALGESIC COMPOUNDS

[75] Inventors: Richard J. Carmosin, Quakertown; John R. Carson, Norristown, both of Pa.

[73] Assignee: McNeilab, Inc., Fort Washington, Pa.

[21] Appl. No.: 850,632

[22] Filed: Apr. 10, 1986

[51] Int. Cl.$^4$ .................. A61K 31/445; C07D 221/04
[52] U.S. Cl. ...................... 514/299; 546/112; 546/334; 546/335; 546/337; 546/340; 546/342
[58] Field of Search .......................... 546/112; 514/299

[56] References Cited

U.S. PATENT DOCUMENTS 4,582,836  4/1986  Carmosin et al. ................... 514/299

OTHER PUBLICATIONS

Chem. Abstracts, p. 1958, cols. 18409–18410, line e.
"Studies on Psychotropic Agents . . . " Chem. Pharm. Bull. 27(5), pp. 1159–1168, Yasutaka Nagai et al., 1979.
"Addition von Aldehyden . . . ", J. Heterocyclic Chem. 14, pp. 573–581, Hermann Stetter et al., Jun. 1977.
"The Structures and Spectral Properties . . . ", vol. 31, pp. 4215–4220, Manfred G. Reinecke et al., Dec. 1966.
"3-Arylquinolizidines, Potential Antidepressant Agents", J. Med. Chem., vol. 18, No. 11, pp. 1126–1130, M. E. Rogers et al., 1975.
"A Synthesis of Octahydropyrrocolines", J. Proc. Royal Soc., vol. 73, pp. 240–252, Francis Lions et al., 1940.

Primary Examiner—Henry R. Jiles
Assistant Examiner—Bernard I. Dentz
Attorney, Agent, or Firm—David J. Levy

[57] ABSTRACT

Octahydroindolizine compounds of formula (I):

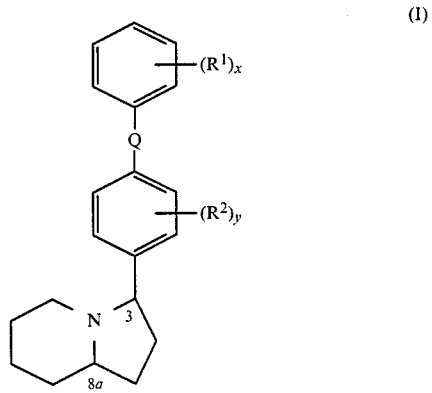

wherein Q is —NR—, —(CH$_2$)$_z$—, —CH=CH—, —C≡C—, —OCH$_2$—, —SCH$_2$—, —SO$_2$—, —SO—, —CO—, or an oxygen or a sulfur atom and where R, R$^1$ and R$^2$ are substituents such as alkyl and x, y and z are independently the integers 0–3. Also, pharmaceutical compositions containing (I), intermediates and methods for treating pain.

14 Claims, No Drawings

3-DIPHENYL SUBSTITUTED OCTAHYDROINDOLIZINE ANALGESIC COMPOUNDS

The present invention comprises certain octahydroindolizine compounds including acid addition salts thereof, methods for their preparation and use, pharmaceutical compositions and intermediates used in their synthesis.

3-Aryloctahydroindolizines are disclosed by I. Murakoshi in Yakugaku Zasshi, 78, pages 594–597 (1958) which appears in Chemical Abstracts at Volume 52, pages 18409b to 18410e (1958); by Y. Nagai et al. in Chem. Pharm. Bull., 27 (5), pages 1159–1168 (1979); and H. Stetter et al. in the Journal of Heterocyclic Chemistry, 14, pages 573–581 (1977). 1-Phenylindolizine is disclosed by M. G. Reinecke et al. in the Journal of Organic Chemistry, 31, pages 4215–4220 (1966). Quinolizidines are shown by M. E. Rogers in the J. of Medicinal Chem. Vol. 18, No. 11, pages 1126–1130 (1975) while octahydropyrrocolines are disclosed by F. Lions in Proc. Royal Soc., N. S. Wales 73, pages 240–252 (1940).

Particular 3-aryloctahydroindolizines are set forth in our U.S. Pat. No. 4,582,836 having an issue date of Apr. 15, 1986.

SUMMARY OF THE INVENTION

Compounds of the present invention are of the following formula (I):

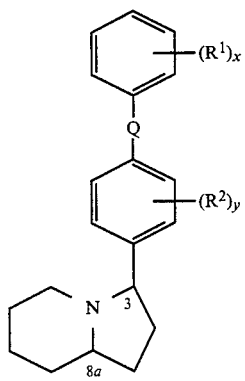

and acid addition salts wherein Q represents —NR—, —(CH$_2$)$_z$—, —CH=CH—, —C≡C—, —OCH$_2$—, —SCH$_2$—, —SO$_2$—, —SO—, —CO—, or an oxygen or a sulfur atom, R, R$^1$ and R$^2$ are substituents such as alkyl, and x, y and z are independently chosen from integers 0-3. Also included within the invention are pharmaceutical compositions and methods for alleviation of pain using the compounds of formula (I) and intermediates used in the preparation of formula (I) compounds.

DETAILED DESCRIPTION OF THE INVENTION

Compounds of the present invention are octahydroindolizines of the following formula (I):

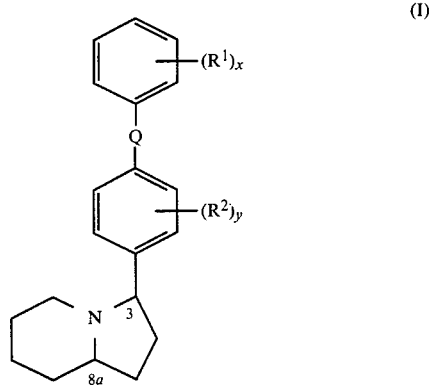

wherein
Q is —NR—, —(CH$_2$)$_z$—, —CH=CH—, —C≡C—, —OCH$_2$—, —SCH$_2$—, —SO$_2$—, —SO—, —CO—, or an oxygen or a sulfur atom;
R is hydrogen or alkyl;
R$^1$ is independently amino, alkylamino, dialkylamino, —SR$^3$, —SOR$^4$, —SO$_2$R$^5$, —COOR$^6$, —COR$^7$, —NR$^8$COR$^9$, alkyl, alkoxy, haloalkyl, nitro, cyano or halo;
R$^2$ is independently alkyl, alkoxy, halo, haloalkyl, alkylthio or cyano;
R$^3$ is hydrogen or alkyl;
R$^4$ is alkyl;
R$^5$ is alkyl;
R$^6$ is alkyl;
R$^7$ is hydrogen or alkyl;
R$^8$ is hydrogen or alkyl;
R$^9$ is hydrogen or alkyl;
x is thee integer 0, 1, 2 or 3;
y is the integer 0, 1, 2 or 3; and
z is the integer 0, 1, 2 or 3
and the pharmaceutically-acceptable acid-addition salts thereof.

In more detail, when Q is —OCH$_2$— or —SCH$_2$—, the oxygen or sulphur atom thereof is in particular attached to the phenyl ring directly attached to the octahydroindolizine moiety. Particular compounds of formula (I) are those wherein Q represents —(CH$_2$)$_z$—, —CH=CH—, —C≡C—, —OCH$_2$— or an oxygen or a sulfur atom.

R, in more detail, is hydrogen or alkyl of about 1 to 4 carbons.

R$^1$, in more detail, is, same or different, amino; alkylamino of about 1 to 4 carbons such as methylamino, ethylamino, and n-propylamino; dialkylamino of about 1 to 4 carbons in each alkyl group such as dimethylamino, ethylmethylamino and diisopropylamino; an —SR$^3$ group, wherein R$^3$ represents a hydrogen atom or an alkyl group of about 1 to 4 carbons; an —SOR$^4$ group, i.e., a sulfoxide, wherein R$^4$ is alkyl of about 1 to 4 carbons; an —SO$_2$R$^5$ group, i.e., a sulfone, wherein R$^5$ is alkyl of about 1 to 4 carbons such as methyl, ethyl, or n-butyl; a —COOR$^6$ group, wherein R$^6$ is alkyl of about 1 to 4 carbons; a —COR$^7$ group, wherein R$^7$ is hydrogen or alkyl of about 1 to 4 carbons; an —NR$^8$COR$^9$ group wherein R$^8$ is hydrogen or alkyl of about 1 to 4 carbons and R$^9$ is hydrogen or alkyl of about 1 to 4 carbons such as methyl or n-butyl; alkyl of about 1 to 4 carbons; alkoxy of about 1 to 4 carbons such as methoxy, ethoxy, n-propoxy and n-butoxy; haloalkyl of about 1 to 4 carbons independently substituted by one or more of fluoro, chloro, bromo or iodo such as trifluoromethyl and 2,2,2-trifluoroethyl; alkylthio of about 1 to 4 carbons such as methylthio or ethylthio; nitro; cyano; or halo such as fluoro, chloro, bromo or iodo. Particular compounds of formula (I) are those wherein $R^1$ is —$NR^8COR^9$ such as —$NHCOCH_3$ and also compounds of formula (I) wherein $R^1$ is in the para position relative to Q.

$R^2$, in more detail, is independently alkyl of about 1 to 4 carbons; alkoxy of about 1 to 4 carbons such as methoxy, ethoxy and iso-propoxy; halo such as fluoro, chloro, bromo or iodo; or haloalkyl of about 1 to 4 carbons independently substituted by one or more of fluoro, chloro, bromo or iodo such as trifluoromethyl and 2,2,2-trifluoroethyl; alkylthio of about 1 to 4 carbons such as methylthio or n-propylthio or cyano.

As used herein, specific examples of the alkyl portions of about 1 to 4 carbons for various groups, e.g. alkyl for R, $R^1$–$R^9$, alkoxy for $R^1$ and $R^2$ and haloalkyl for $R^1$ and $R^2$, are methyl, ethyl, n-propyl, iso-propyl, n-butyl, sec-butyl, iso-butyl and tert-butyl.

In more detail, x, y and z represent, independently, the integers 0, 1, 2 or 3. A particular value for x is the integer 1. Particular values for y are 0 and 1.

Particular compounds of the invention include the following:
N-4-[[4-(octahydro-3-indolizinyl)phenyl]thio]phenyl]acetamide;
N-[3-[[4-(octahydro-3-indolizinyl)phenyl]ethynl]-phenyl]acetamide;
3-[4-(phenylmethoxy)phenyl]octahydroindolizine;
N-[3-[2-[4-(octahydro-3-indolizinyl)phenyl]ethenyl]-phenyl]acetamide;
octahydro-3-[4-(phenylethynyl)phenyl]indolizine;
octahydro-3-[4-(2-phenylethyl)phenyl]indolizine;
3-[4-[(4-methylphenyl)thio]phenyl]octahydroindolizine;
3-[4-[(4-chlorophenyl)thio]phenyl]octahydroindolizine;
N-[3-[2-[4-(octahydro-3-indolizinyl)phenyl]ethyl]-phenyl]acetamide;
3-[[4-(octahydro-3-indolizinyl)phenyl]thio]benzenamine;
N-[3-[[4-(octahydro-3-indolizinyl)phenyl]thio]phenyl]acetamide;
N-[4-[4-(octahydro-3-indolizinyl)phenoxy]phenyl]acetamide; and
N-[4-[[3-chloro-4-(octahydro-3-indolizinyl)phenyl]thio]phenyl]acetamide.

Various isomers are possible in formula (I) compunds and the present invention includes all such individual enantiomers, diasteromers, racemates and other isomer ratios. Specifically such compounds may exist in the following forms: trans racemic, trans (+), trans (−), cis racemic, cis (+) and cis (−). Optical isomers of the compounds of this invention may be obtained by conventional resolution techniques known to those skilled in the art of organic chemistry. For example, addition of an optically active acid, e.g. (+) or (−) tartaric acid, (+) or (−) camphor sulfonic acid, (+) or (−) mandelic acid or (+) or (−) p-toluoyltartaric acid to the free base of the compounds of this invention to produce a mixture of two diastereometric salts. Separation of the diastereometric salts by conventional methods such as fractional crystallization and liberation of the free bases from the individual salts provides the individual enantiomeric free bases.

Representative salts of the compounds of formula (I) which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, 2-acetoxybenzoic or a salt made with saccharin. Such salts can be made by reacting the free base of (I) with the acid and recovering the salt.

Compounds of this invention may be prepared by methods selected from the following four Routes (A), (B), (C) and (D).

Route (A):

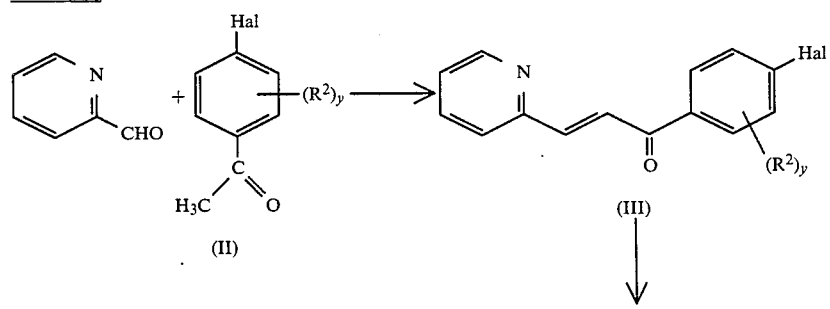

-continued
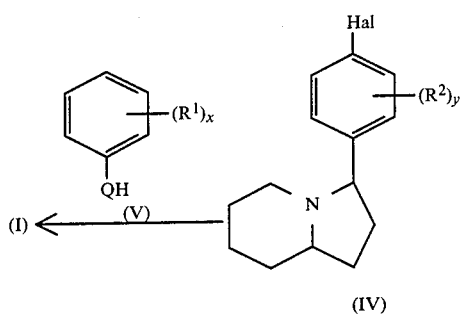
Route (B):
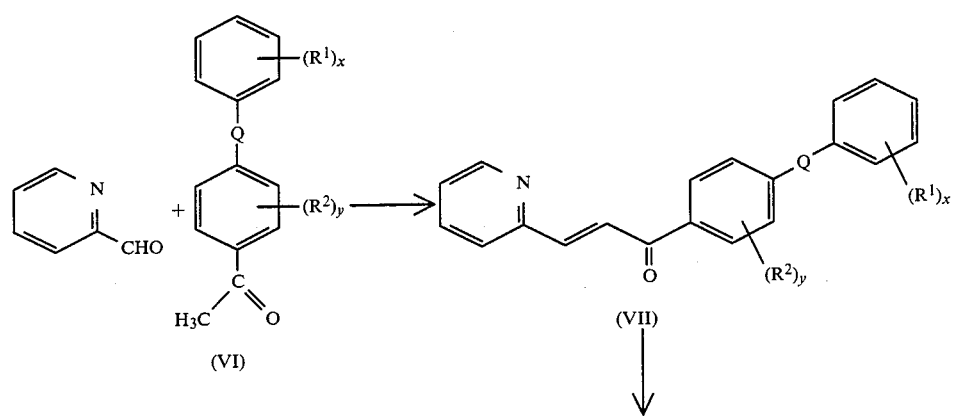
Route (C):
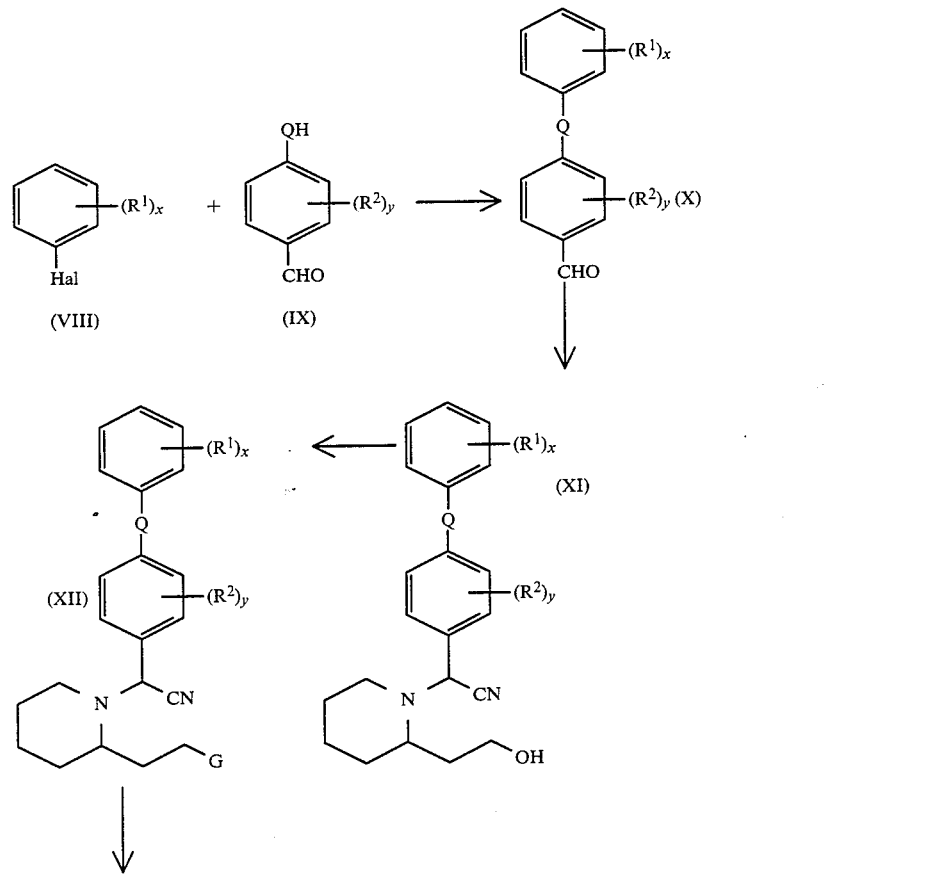

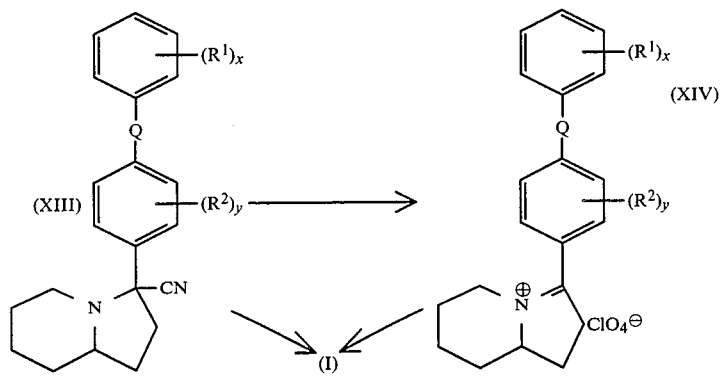

Route (D):

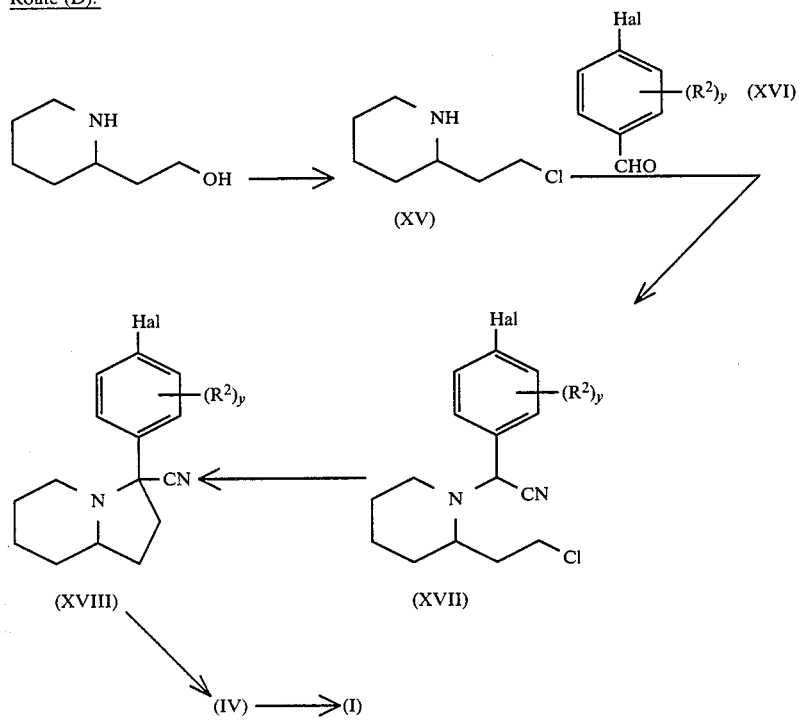

In the first Route (A), pyridine-2-carboxaldehyde is condensed with an appropriate $(R^2)_y$-substituted 4-haloacetophenone of formula (II) to produce a chalcone of structure (III). The condensation reaction may be carried out under Claisen-Schmidt conditions, for instance in a lower alkanol solvent, at a temperature of about −30° to 50° C., preferably at about 10° C. in the presence of an alkali metal hydroxide. Alternatively, the condensation may be brought about under Knoevenagel conditions: ammonia or a primary or secondary amine catalyst and a carboxylic acid. For instance, piperidine in acetic acid at an elevated temperature of about 50° to 100° C. will effect the condensation. Catalytic hydrogenation and concurrent cyclization of the chalcone affords a 3-(4-halophenyl)octahydroindolizine of formula (IV), wherein Hal is fluoro, chloro, bromo or iodo. The hydrogenation may be carried out over a noble metal, e.g. platinum, palladium, rhodium or ruthenium, preferably platinum or rhodium on carbon. An alkanoic acid or a lower alkanol may be used as solvent. A mineral acid such as hydrogen chloride or perchloric acid may be present to promote the reaction. The hydrogenation/cyclization may be carried out at from room temperature to about 100° C. at hydrogen pressures ranging from about 30 psi to about 3000 psi. The 3-(4-halophenyl)octahydroindolizine of formula (IV) is then condensed with an HQ-substituted phenyl compound bearing an appropriate $(R^1)_x$ group of formula (V) to produce a 3 -substituted octahydroindolizine of formula (I). The condensation reaction is carried out in the presence of a base and a palladium catalyst. Typical bases include alkali metal alkoxides or hydroxides, sodium hydride, sodamide or other alkali metal amides or alkyl amines. The palladium catalysts employed include Pd(OAc)$_2$, (Ph$_3$P)$_4$Pd and (Ph$_3$P)$_2$Cl$_2$Pd. Temperatures in the range of about 25° to about 150° C. are generally employed and the reaction is run in a solvent such as butanol, DMF, THF or triethylamine. Alternatively, the condensation of (IV) with (V) to produce (I) may be carried out in the presence of a base and Cu$_2$O in a dipolar aprotic solvent such as DMF, quinoline or methyl pyrrolidine at temperatures of about 75° to about 200° C. When Q is —C≡C—, i.e., an acetylene, the condensation of (IV) with (V) to produce (I) is carried out with a palladium catalyst as above in the presence of a base such as trialkylamine or sodium hydroxide under phase transfer conditions. Compounds of formula (I) wherein Q is —CH=CH—or —(CH$_2$)$_z$— and z is 2 or 3 may be prepared from the corresponding acetylenes or olefins, respectively by hydrogenation methods known to those skilled in the art of organic chemistry such as selective catalytic hydrogenation over a noble metal catalyst. Lindlar conditions may be employed to produce cis-olefins of compounds of formula (I). Route (A) is preferably employed to prepare products of formula (I) where Q is —C≡C— or —S—.

In the second Route (B), a 4-substituted acetophenone of formula (VI) wherein Q is particularly —OCH$_2$—, —NR— or —O— is condensed with pyridine-2-carboxaldehyde under either Claisen-Schmidt or Knoevenagel conditions as described in Route (A) to produce a corresponding 4-substituted phenyl chalcone of formula (VII). The chalcone is then cyclized to the corresponding octahydroindolizine of formula (I) wherein Q is —OCH$_2$—, —NR— or —O— using the hydrogenation/cyclization conditions described in Route (A) above.

In the third Route (C) to prepare compounds of formula (I), an appropriate (R$^1$)$_x$-substituted halobenzene of formula (VIII) is condensed with the anion of an appropriate HQ—(R$^2$)$_y$-substituted benzaldehyde of formula (IX) to produce an aldehyde of formula (X), wherein Q represents —CH$_2$O—, —CH$_2$S—, —NR— or a sulfur or an oxygen atom. With Q=—CH$_2$O— or —CH$_2$S—, the final products (I) will have the oxygen or sulphur attached through the —CH$_2$— group to the phenyl ring directly attached to the octahydroindolizine using this method. The anion of (IX) may be conveniently formed by the action of an alkali metal hydride such as sodium hydride at a temperature range of about 0° to about 25° C. Anion formation and subsequent alkylation takes place readily in a polar aprotic solvent such as N,N-dimethylformamide or dimethylsulfoxide. The aldehyde of formula (X) is then reacted with piperidine-2-ethanol and an alkali metal cyanide such as sodium cyanide to produce a hydroxy nitrile of formula (XI). Nitrile formation generally takes place in a protic solvent such as water or a lower alkanol at a temperature of about 0° to about 50° C. The hydroxy nitrile is converted by the action of thionyl chloride, methane sulfonyl chloride or toluene sulfonylchloride to give a nitrile to formula (XII) where the group G is a leaving group such as chloro, methanesulfonyl or p-toluenesulfonyl respectively. Treatment of the nitrile (XII) with a strong base, for instance, sodium hydride in DMF, gives a 3-cyano-3-substituted octahydroindolizine of formula (XIII). The conversion of (XIII) to a target compound of formula (I) may be carried out by treatment of (XIII) with perchloric acid to give an octahydroindolizinium perchlorate of formula (XIV) which is transformed to the desired product (I) by catalytic hydrogenation over a noble metal catalyst, for instance platinum or by direct reduction of (XIII) with a hydride reducing agent, such as NaBH$_4$, NaBH$_3$CN or LiAlH$_4$. Route C is preferred for the preparation of compounds of formula (I) wherein Q is —CH$_2$O—, —CH$_2$S—and —S—.

In the fourth Route (D), piperidine-2-ethanol is first reacted with thionyl chloride, to produce the corresponding chloro substituted piperidine of formula (XV). The piperidine of formula (XV) is then reacted with an (R$^2$)$_y$-substituted-4-halobenzaldehyde of formula (XVI) in the presence of an alkali metal cyanide such as sodium cyanide in a polar solvent such as water at a temperature of about 0° to about 50° C. with about 20° C. preferred to produce a 4-halophenyl substituted nitrile of formula (XVII). The nitrile of formula (XVII) is then cyclized by the action of a strong base such as sodium hydride or sodamide in a dipolar aprotic solvent such as DMF to give a 3-cyano-3-substituted octahydroindolizine of formula (XVIII). Reaction of (XVIII) with a reducing agent such as LiAlH$_4$ produces a 3-(4-halophenyl)octahydroindolizine of formula (IV). The halo compound (IV) is then reacted with an HQ-substituted phenyl compound of formula (V) following the procedure outlined in Route (A) to produce a product octahydroindolizine of formula (I).

In each of the Routes (A), (B), (C) and (D), a mixture of diastereomers is produced in which the biologically more active 3-alpha, 8a-beta diastereomer is predominant. The diastereomers may be separated by chromatography on silica or by fractional crystallization.

Also included within the present invention are intermediates that are useful in the preparation of compounds of formula (I), e.g. (VII), (XIII) and (XVI) where the various substituents, groups and values such as Q, R, R$^1$, R$^2$, R$^3$, R$^4$, R$^5$, R$^6$, R$^7$ R$^8$ and R$^9$ and x, y and z are as defined herein for the formula (I) compounds including the isomeric considerations.

The groups R$^1$ and R$^2$ may be attached directly to their respective phenyl rings during the synthesis of the octahydroindolizine ring. Alternatively they may be attached following the synthesis of the octahydroindolizine of formula (I). For instance, an R$^1$ or R$^2$ halo-substituted octahydroindolizine may be converted to the corresponding lithium derivative by reaction with an alkyllithium. The lithium derivative on raction with dimethyldisulfide affords the corresponding methylthio octahydroindolizine of formula (I). An R$^1$ or R$^2$ halo-substituted octahydroindolizine of formula (I) when subjected to palladium catalyzed coupling with cuprous cyanide or a 1-alkyne gives the corresponding R$^1$ or R$^2$ substituted cyano or alkynyl derivative.

The activity of compounds of the invention as analgesics may be demonstrated by the mouse acetylcholine-bromide induced constriction assay as described below:

Mouse Acetylcholine-Bromide-Induced Abdominal Constriction Assay

The mouse acetylcholine-induced abdominal constriction assay, as described by Collier et al. in Brit. J. Pharmacol. Chem. Ther., 32: 295–310, 1968, with minor modifications was used to assess analgesic potency of the compounds of formula (I). The test drugs or appropriate vehicle were administered orally (p.o.) and 30 minutes later the animals received an intraperitoneal (i.p.) injection of 5.5 mg/kg acetylcholine bromide (Matheson, Coleman and Bell, East Rutherford, NJ). The mice were then placed in groups of four into glass bell jars and observed for a ten minute observation period for the occurrence of a writhe (defined as a wave of constriction and elongation passing caudally along the abdominal wall, accompanied by a twisting of the trunk and followed by extension of the hind limbs). The percent inhibition of writhing (equated to % analgesia) was calculated as follows: The % Inhibition of writhing, i.e., % analgesia is equal to the difference between the No. of control animals writhing and the No. of drug-treated animals writhing times 100 divided by the No. of control animals writhing.

At least 20 animals were used for control and in each of the drug treated groups. Four doses were used to determine each dose response curve and $ED_{50}$ (that dose which inhibits writhing by 50%). The $ED_{50}$ values and their 95% fiducial limits were determined by a computer assisted probit analysis.

TABLE I

Mouse Acetylcholine-Bromide Induced Abdominal Constriction Assay

| Compound of Example No. | $ED_{50}$ |
| --- | --- |
| 1c | 2.8 |
| 1d | 3.4 |
| 1e | 4.5 |
| 2 | 17.6 |
| 3b | 16.8 |
| 4 | 6.9 |
| 6 | 6.9 |
| 7 | 20-30 |
| 8a | 3.2 |
| 8c | 12.4 |
| 9 | 86% @ 30 mg/kg |
| 11 | 73% @ 30 mg/kg |
| 12f | ≦5 |
| 13e | 46% @ 30 mg/kg |

Based on the above results, invention compounds of formula (I) may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient.

In the following Examples and throughout the specification, the following abbreviations may be used: mg (milligrams); g (grams); kg (kilograms); mL (milliliters); mmole (millimoles); M (molar); N (normal); atm (atmospheres); psi (pounds per square inch); mp (melting point); bp (boiling point); meq (milliequivalents); E (trans); Z (cis); $Et_2O$ (diethylether); EtOAc (ethyl acetate); Ac ($-COCH_3$); MeOH (methanol); EtOH (ethanol); LAH (lithium aluminum hydride); THF (tetrahydrofuran); DMF (dimethylformamide); p.o. (per os, orally); i.p. (intraperitoneal); hplc (high pressure liquid chromatography; hr (hours); min (minutes); and C,H,H,O, etc. (the chemical symbols for the elements). Unless otherwise indicated, all temperatures are reported in °C. (degrees centigrade) and all references to ether are to $Et_2O$.

EXAMPLE 1 a. 1-(4-Bromophenyl)-3-(2-pyridinyl)-2-propen-1-one Hydrochloride

A 50 g (0.47 mole) sample of pyridine-2-carboxaldehyde was added in portions of a solution of 100 mL of 10% sodium hydroxide and 50 mL of MeOH at 10° C. A solution of 50 g (0.25 mole) of 4-bromoacetophenone in 300 mL of MeOH was added in portions over 2 hr at 20° C., the the mixture was stirred for an additional hour at 10° C. The solid was filtered, and partitioned between ether and water. The ether layer was washed with brine, dried ($MgSO_4$), and the filtrate was treated with ethereal hydrogen chloride. The salt was recrystallized from absolute ethanol, and then recrystallized from MeOH to give 50 g (62% yield) of the title compound, mp 208°–210° C.

b.

trans-3-(4-Bromophenyl)octahydroindolizine Hydrochloride

A solution of 22.8 g (0.079 mole) of the free base of the product of Example 1a in 228 mL of glacial acetic acid was hydrogenated over 228 mg of platinum oxide at 50 psi for 1 day. The reduction was recharged with 229 mg of platinum oxide and continued for 1 more day at 50 psi. The catalyst was filtered, and the solvent evaporated under reduced pressure to an oil. The oil was partitioned between ether and 10% sodium hydroxide. The ether layer was dried (MgSO$_4$) and the ether evaporated under reduced pressure to an oil. The oil was distilled in a kugelrohr at 100°–120° C. at 0.005 mm Hg to give an oil. The oil was treated with ethereal HCl and the salt was recrystallized from acetonitrile to give 2 g of the title compound, mp=234°–236° C.

c.

trans-N-[4-[4-(Octahydro-3-indolizinyl)phenyl]thio]-phenyl]acetamide Hydrochloride Hydrate A solution of 11.9 g (0.073 mole) of 4-acetamidothiophenol in 180 mL of dry n-butanol was added dropwise to 0.073 mole of sodium hydride (from 3.5 g of 50% sodium hydride washed with hexane to remove the oil) and 60 mL of dry n-butanol. Then a solution of 26.5 g (0.073 mole) of trans-3-(4-bromophenyl)octahydroindolizine in 60 ml of dry n-butanol and 3.2 g of tetrakistriphenylphosphine palladium (O) were added to the mixture, and the reaction mixture refluxed with stirring overnight. The reaction mixture was cooled to room temperature and the solvent evaporated in vacuo to an oil. The oil was partitioned between water and ether, and the ether layer was washed with brine, dried (K$_2$CO$_3$), and the ether evaporated in vacuo to a red oil. The oil was flash chromatographed on SiO$_2$ using 85% hexane, 14% acetone as the eluant. The product containing fractions were pooled, and evaporation of the solvent gave a solid. The solid was recrystallized from EtOAc-hexane to give 12 g of a solid. The solid was dissolved in ether and treated with ethereal HCl to give the salt. The salt was dried in vacuum oven overnight to give 11.5 g (30% yield) of the title compound as white solid, mp=170°–173° C.

d.

(+)N-[4[[4-(trans-Octahydro-3-indolizinyl)phenyl]thio]phenyl]acetamide Hydrochloride Hydrate The resolution of 122 g (0.44 mole) of racemic trans-3-(4-bromophenyl)octahydroindolizine was done by adding 176.4 g (0.44 mole) of (+)-di-p-toluoyl-D-tartaric acid in iso-propanol and allowing the salt to crystallize slowly for four days. The salt that precipitated out was then recrystallized from 95% EtOH. The first crop that crystallized from 95% EtOH was filtered to give 49.8 g (24% yield) of the (+) diastereoisomer which had an $[\alpha]_{25}{}^D = +120$.

To a sample of 0.035 mole of sodium hydride (from 1.7 g of 50% sodium hydride washed free of oil with hexane) was added 40 mL of n-butanol and the mixture stirred until all the NaH dissolved. Then a solution of 5.7 g (0.035 mole) of 4-acetamidothiophenol in 100 mL of n-butanol was added and the mixture stirring for 20 min. A solution of 12.7 g (0.035 mole) of resolved (+) trans-3-(4-bromophenyl)octahydroindolizine in 4 mL of n-butanol and 1.6 g of tetrakistriphenylphosphine palladium (O) was added and the mixture allowed to reflux overnight. Then the reaction mixture was cooled and the solid filtered. The solvent was evaporated in vacuo, and the oil residue was partitioned between water and ether. The ether layer was washed with water, brine and dried (K$_2$CO$_3$). The ether was evaporated in vacuo to a red oil. The oil was flash chromotagraphed on SiO$_2$ using 86% hexane, 14% EtOAc as the eluant. The product bearing fractions were pooled and the solvent evaporated in vacuo to an oil. The oil was treated with ethereal HCl to give 5.94 g (53.6% yield) of the title compound as a solid, mp=178°–180° C.; $[\alpha]_{25}{}^D$.

e.

(−)N-[4[[4-(trans-Octahydro-3-indolizinyl)phenyl]thio]phenyl]acetamide Hydrochloride Hydrate The mother liquors from the resolution in example 1d were concentrated in vacuo. The free base was made by partitioning the residue between 3N sodium hydroxide and diethyl ether. The ether layer was dried over potassium carbonate and was evaporated in vacuo. This residue was distilled in a kugelrohr at 0.005 mm Hg between 70°–110° C. The 114.3 g (0.408 moles) of distillate collected was combined with 165 g (0.408 moles) (−)-di-p-toluoyl-D-tartaric acid in methanol and the salt was allowed to crystallize slowly for four days. The salt that precipitated out was recrystallized from MeOH. It was filtered to give 82.5 g (30% yield) of the (−)diastereoisomer; $[\alpha]_{25}{}^D = -119°$, mp=191°–195° C.

To a sample of 0.36 mole of sodium hydride (1.7 g of 50% sodium hydride washed free of oil with hexane) was added 40 mL of n-butanol and the mixture stirred until all the NaH dissolved. Then a solution of 5.9 g (0.036 moles) of 4-actamidothiophenol in 100 mL of n-butanol was added and the mixture stirred for 20 min. A solution of 10 g (0.036 moles) (−)-trans-3-(4-bromophenyl)octahydroindolizine in 40 mL of n-butanol and 1.8 g of tetrakistriphenylphosphine palladium (O) was added and the mixture allowed to reflux overnight. Then the reaction mixture was cooled and the solid filtered. The solvent was evaporated in vacuo, and the oily residue was partitioned between water and EtOH. The ether layer was washed with water, brine and dried (K$_2$CO$_3$). The ether was evaporated in vacuo to a red oil. The oil was flashed chromatographed on SiO$_2$ using 86% hexane, 14% EtOAc as the elutant. The product bearing fractions were pooled and the solvent evaporated in vacuo to an oil. The oil was treated with etheral hydrogen chloride to give 5.2 g (39% yield) of the title compound as a solid, mp=176°–183° C.; $[\alpha]_{25}{}^D = -22.4°$.

EXAMPLE 2

N-[3-[[4-(trans-Octahydro-3-indolizinyl)phenyl]ethynyl]phenyl]acetamide

A 10 g (0.036 mole) sample of trans-3-(4-bromophenyl)octahydroindolizine and 6.8 g (0.43 mole) of 3-ethynylphenylacetamide were added to a mixture of 12 mL of dry triethylamine and 88 mL of dry THF under argon. To this solution was added 0.041 g (0.21 mmol) of cuprous iodide and 0.495 g (0.428 mmol) of tetrakistriphenylphosphine palladium (O) and the mixture refluxed overnight. Then an additional 3.4 g (0.021 mole) of 3-ethynylphenylacetamide and 0.02 g (0.11 mole) of cuprous iodide and 0.247 g (0.21 mmole) of tetrakistriphenylphosphine palladium (O) was added and the mixture refluxed overnight. Then the reaction was cooled to room temperature, filtered, and the solvent evaporated in vacuo to give 13.4 g of a solid residue. The solid was flash chromatographed on SiO$_2$ using 50% EtOAc/50% chloroform as the eluant. The first major compound bearing fractions were pooled and the solvent evaporated in vacuo to give 5.2 g of a solid. The solid was crystallized from toluene, and recrystallized from 1,2-dichloroethane to give 2.8 g (12% yield) of the title compound as a light tan solid, mp=161°–163° C.

EXAMPLE 3 a.

1-[4-(Phenylmethoxy)phenyl]-3-(2-pyridinyl)-2-propen-1-one

A sample of a 42.4 g (0.4 mole) of pyridine-2-carboxaldehyde was added to a solution of 83.6 mL of 10% sodium hydroxide and 100 mL of DMF at 10° C. Then a solution of 47.2 g (0.21 mole) of 4-benzyloxyacetophenone in 300 mL of DMF was added slowly over a period of 1 hr to the mixture keeping the temperature of the reaction mixture at 5°–13° C. After 1.5 hr, the reaction mixture was allowed to warm to room temperature. Water was added, and the product precipitated out as a solid. The solid was crystallized from 95% ethanol to give 48.2 g (73% yield) of the title compound as a yellow solid, mp=131°–134° C. An additional 3.3 g (5% yield) of the product was obtained from the mother liquor, mp=131°–134° C.

b.

trans-Octahydro-3-[4-(phenylmethoxy)phenyl]indolizine Hydrochloride

A 49.2 g (0.16 mole) sample of the product of Example 3a was dissolved in 490 mL of glacial acetic acid and added to 4.82 g of 5% rhodium on carbon and placed on a Parr apparatus under a pressure of 50 psi of hydrogen. After 2 days, the theoretical amount of hydrogen had been taken up by the reaction mixture. The catalyst was removed by filtration, and the acetic acid solution basified with 10% sodium hydroxide and extracted with ether. The ether layer was washed with brine, dried (K$_2$CO$_3$), and the ether evaporated in vacuo to give 29.3 g of an orange oil. The oil was chromatographed on the Waters Prep 500 preparative hplc using 90% hexane, 10% EtOAc. The first major compound bearing fractions were pooled and the solvent evaporated in vacuo to give 19.3 g (42% yield) of the free base of the title compound as an oil. A 9.5 g sample of this oil was dissolved in acetonitrile and treated with ethereal HCl to give 9.2 g of the salt as a white solid. The solid was recrystallized from acetonitrile to give 8.25 g of the title compound as a white solid, mp=205°–209° C.

EXAMPLE 4

N-[3-[2(Z)-[4-trans-Octahydro-3-indolizinyl)phenyl]ethenyl]phenyl]acetamide (E)-2-Butenedioate A 2.68 g (7.5 mmole) sample of the product of Example 2 was dissolved in 27 mL of pyridine and 81.6 mg of 5% palladium on barium sulfate was added. The mixture was placed on an atmospheric pressure hydrogenation apparatus at 1 atm pressure of hydrogen and after 1 night the reaction mixture consumed 22 mL of hydrogen. An additional 81.6 mg of 5% palladium on barium sulfate was added and after running one night more, the reaction mixture had consumed 150 ml of hydrogen. The mixture was filtered, and the pyridine evaporated in vacuo to a green oil. The oil was treated with dry ether and a flocculant precipitate was filtered off. The oil was dissolved in ethanol and 0.71 g of fumaric acid added. The solid fumaric acid salt was recrystallized twice from absolute ethanol to give 1 g (28% yield) of the title compound as a white solid, mp 157°–159° C.

EXAMPLE 5 trans-Octahydro-3-[4-(phenylethynyl)phenyl]indolizine

A 27.7 g (0.099 mole sample of trans-3-(4-bromophenyl)octahydroindolizine was dissolved in a mixture of 55 mL of triethylamine and 225 mL of dry THF under an atmosphere of argon and 12.1 g (0.12 mole) of phenylacetylene was added. Then 2.3 g (2 mmol) of tetrakistriphenylphosphine palladium (O) and 0.75 g 3.9 mmol) of cuprous iodide were added to the reaction mixture and the reaction refluxed overnight. An additional 1.2 g (1 mmol) of tetrakistriphenylphosphine palladium (O) and 0.38 g (1.9 mmol) of cuprous iodide were added to the reaction mixture and the mixture allowed to reflux overnight. The reaction was allowed to cool to room temperature, the mixture was filtered, and the THF evaporated in vacuo to a brown oil. The oil was partially dissolved in EtOAc and the insoluble material was filtered off. The EtOAc was evaporated in vacuo to an oil. The oil was flash chromatographed using 99% hexane, 1% EtOAc as the eluant. The major product bearing fractions were pooled, and the solvent evaporated in vacuo to give 12.5 g (42% yield) of the title compound as an oil.

EXAMPLE 6 trans-Octahydro-3-[4-(2-phenylethyl)phenyl]indolizine Hydrochloride

A 12.5 g (0.042 mole) sample of the product of Example 5 was dissolved in 100 mL of glacial acetic acid and 125 mg of platinum oxide was added. The mixture was placed on a Parr apparatus at 50 psi pressure of hydrogen and allowed to run overnight. The decrease in hydrogen pressure was 46.7 psi. An additional 125 mg of platinum oxide was added to the reaction mixture and the hydrogenation continued overnight at 50 psi of hydrogen. The mixture was then filtered, and the acetic acid evaporated in vacuo. The oil residue was partitioned between 10% sodium hydroxide and ether, and the ether layer was dried (K$_2$CO$_3$) and evaporated in vacuo to give an oil. The oil was dissolved in isopropanol and treated with ethereal HCl to give the salt as a white solid. The solid was recrystallized from acetonitrile twice and again from EtOH/Et$_2$O to give 1.5 g (10.6% yield) of the title compound as a white solid, mp=191°–193° C.

EXAMPLE 7

3-[4-[(4-Methylphenyl)thio]phenyl]octahydroindolizine Hydrochloride

A solution of 0.03 mole of sodium n-butoxide in n-butanol was prepared by adding 15 mL of n-butanol to 0.03 mole of sodium hydride (1.5 g of 50% sodium hydride washed free of oil with hexane) under an atmosphere of argon. A solution of 2 g (0.016 mole) of 4-thiocresol in 175 mL of dry n-butanol was added to the sodium butoxide solution. Then a solution of 4.4 g (0.0157 mole) of trans-3-(4-bromophenyl)octahydroindolizine and 0.76 g (0.0628 mmol) of tetrakistriphenylphosphine palladium (O) were added to the mixture. The reaction mixture was refluxed overnight. Then the reaction mixture was cooled to room temperature, filtered, and the n-butanol was evaporated in vacuo to give an oil. The oil was flash chromatographed on $SiO_2$ using 85% hexane, 15% EtOAc, and the first major product bearing fractions were pooled and the solvent evaporated in vacuo to give an oil residue. The oil was treated with ethereal HCl to give the salt as a solid. Crystallized from acetonitrile, and recrystallized from ispropanol to give 1.83 g (33% yield) of the title compound as a light tan solid, mp=203°-205° C.

EXAMPLE 8 a.

trans-3-[4-[(4-Chlorophenyl)thio]phenyl]octahydroindolizine Hydrochloride

A solution of 4.1 g (0.028 mole) of 4-chlorothiophenol in 40 mL of dry N-methylpyrrolidinone was added to 0.028 mole of sodium hydride (from 1.36 g of 50% sodium hydride washed free of oil with hexane) under an atmosphere of nitrogen. Then a solution of 5.3 (0.019 mole) of trans-3-(4-bromophenyl)octahydroindolizine in 50 mL of dry N-methylpyrrolidinone and 1.35 g of cuprous oxide was added to the mixture and the reaction mixture was refluxed overnight. Then the reaction was cooled to room temperature. MeOH was added, and the mixture was filtered. The solvent was evaporated in vacuo to a brown oil. The oil was flash chromatographed in $SiO_2$ using 98% hexane, 2% acetone as the eluant. The product was collected in fractions 6 and 7, and evaporation of the solvent in vacuo gave an oil. The oil was treated with ethereal HCl to give a solid salt. The solid was recrystallized from acetonitrile to give 77 g (10% yield) of the title compound as a white solid, mp=198°-201° C.

b.

R-(R*,R*)-trans-Octahydro-3-(4-bromophenyl)indolizine 122 g (0.43 moles) of racemic trans-octahydro-3-(4-bromophenyl)indolizine and 176.4 g (0.43 moles) (+)-di-p-toluoyl-D-tartaric acid monohydrate were combined in a minimum amount of boiling iso-propanol. The solution was allowed to sit undisturbed for four days. It was then placed in a freezer overnight. The solid was filtered off and recrystallized once from 95% ethanol. The free base was made by partitioning between $Et_2O$ and 10% sodium hydroxide. The free base was converted to the hydrochloride salt with ethereal HCl and recrystallized from acetonitrile to give 25.9 g of R-(R*,R*)-trans-octahydro-3-(bromophenyl)indolizine (37%) mp=241°-244° C. $[\alpha]_{25}^D = +117.8$.

c.

R-(R*,R*)-trans-3-[4-[(4-Chlorophenyl)thiophenyl]octahydroindolizine Hydrochloride 0.3 g (6.1 mmole) of 50% sodium hydride in oil was placed in a round bottom flask under argon atmosphere. The oil was washed away with hexane. 10 mL of dry deoxygenated n-butanol was added dropwise. The solution was stirred twenty minutes. 0.88 g (6.1 mmoles) p-chlorothiophenol in 20 mL dry, deoxygenated n-butanol was added. The solution was stirred for twenty minutes. 1.7 g (6.1 mmoles). R-(R*,R*)-trans-octahydro-3-(4-bromophenyl)indolizine in 10 mL dry, deoxygenated n-butanol was added. 0.27 g (4 mole%) tetrakistriphenylphosphine palladium (O) was immediately added. The reaction mixture was refluxed under argon overnight. The reaction mixture was cooled, filtered and the filtrate was evaporated in vacuo leaving a brown oily residue. The residue was taken up in diethyl ether, washed with water, brine, and dried over potassium carbonate. The solvent was evaporated in vacuo. The dark oily residue was flashed chromatographed using silica gel as the solid phase and 1% EtOAc in hexane as the eluant. The solvent was evaporated from the fractions containing the desired product. The hydrochloride salt was made from ethereal HCl and recrystallized from acetonitrile. 435 mg of R-(R*,R*)-trans-3-[4-[(4-chlorophenyl)thiophenyl]octahydroindolizine hydrochloride was recovered (21%). mp=173°-174° C. $[\alpha]_{25}^D = +73.7$.

EXAMPLE 9

N-[3-[2-[4-(trans-Octahydro-3-indolizinyl)phenyl]ethyl]phenyl]acetamide

A solution of 3.69 g (0.0103 mole) of the product of Example 2a in 50 mL of acetic acid was added to 0.074 g of platinum oxide and the mixture placed on the Paar apparatus under 50 psi pressure of hydrogen and allowed to run for 1.5 hr. The reaction mixture had consumed 14 psi of hydrogen. The mixture was filtered, and the acetic acid was evaporated in vacuo to an oil. The oil was partitioned between 10% sodium hydroxide and chloroform, the chloroform layer was dried ($K_2CO_3$), and the chloroform was evaporated to give a crystalline solid. The solid was recrystallized from toluene to give 2.8 g of a white solid. The solid was then flash chromatographed using 75% hexane, 25% acetone as the eluant. The first major product containing fractions are pooled, and the solvent evaporated in vacuo to a solid residue. The solid was recrystallized twice from toluene to give 1.37 g (37% yield) of the title compound as a white solid, mp"151.5°-153° C.

19

EXAMPLE 10

3-[[4-(trans-Octahydro-3-indolizinyl)phenyl]thio]-benzeneamine

A solution of 2 g (0.016 mole) of 3-aminothiophenol in 25 mL of dry DMF was added to 0.016 mole of sodium hydride (from 0.77 g of 50% sodium hydride washed with hexane to remove the oil). After all the sodium hydride has reacted, a solution of 2.8 g (0.01 mole) of trans-3-(4-bromophenyl)octahydroindolizine in 20 ml of dry DMF and 0.72 g (0.005 mole) of cuprous oxide were added. The mixture was refluxed overnight. Then an additional 0.35 g (0.002 mole) of cuprous oxide was added to the reaction mixture, and the mixture was refluxed for two days. The reaction was the cooled to room temperature, filtered and the DMF evaporated in vacuo to give a brown oil. The oil was flash chromatographed in $SiO_2$ using 75% hexane, 25% EtOAc as the eluant. The product bearing fractions were pooled and the solvent evacuated in vacuo to give 1.5 g (46% yield) of the title compound as a red oil.

EXAMPLE 11

N-[3-[[4-trans-Octahydro-3-indolizinyl)phenyl]thio]-phenyl]acetamide Hydrochloride Hydrate A sample of 1.4 g (0.004 mole) of the product of Example 10 was added to 5 mL of acetic anhydride and heated on the steam bath for 10 min. The acetic anhydride was then evaporated in vacuo, and the oil residue partitioned between 10% sodium hydroxide and ether. The ether layer was dried ($K_2CO_3$) and the ether evaporated in vacuo to a yellow oil. The oil was treated with ethereal hydrogen chloride, and the solid salt was recrystallized from 1% water-acetonitrile to give 0.4 (22% yield) of the title compound as a tan solid, mp=201°–204° C.

EXAMPLE 12 a.

4-(4-Nitrophenoxy)benzaldehyde

A solution of 61 g (0.5 mole) of 4-hydroxybenzaldehyde in 20 mL of dry DMF was added to a suspension of 0.5 mole of sodium hydride (from 24 g of 50% sodium hydride washed free of oil with hexane) in 500 mL of DMF. When the sodium hydride had completely dissolved, a solution of 53 mL (0.55 mole) of 4-fluoronitrobenzene was added and the reaction mixture was heated to 70°–80° C. for 2 hr. The mixture was then poured into water, the solid collected and recrystallized from iso-propanol. The solid was recrystallized again from ethanol to give 88 g (85% yield) of the title compound as a yellow solid, mp=101°–104° C.

b.

2(2-Hydroxyethyl)alpha-[4-(4-nitrophenoxy)phenyl]-1-piperidineacetonitrile

A sample of 81.7 g (0.38 mole) of the product of Example 12a was added to a solution of 46.4 g (0.38 mole) of 2-hydroxyethylpiperidine and 46.8 g (0.72 mole) of potassium cyanide in 120 mL (0.38 mole) of 3N hydrochloric acid and the mixture stirred at room temperature for two days. The oil that separated out was partitioned between water and chloroform, the chloroform layer was washed with brine, dried ($Na_2SO_4$), and the chloroform evaporated in vacuo to give 126 g of the crude title compound as a red oil.

c.

2-[1-[(Cyano[4-[4(4-nitrophenoxy)phenyl]methyl]-2piperidinyl]ethyl 4-Methylbenzenesulfonate A 16.1 g (0.085 mole) sample of p-toluenesulfonyl chloride was added in portions to a cooled solution of 32.4 g (0.085 mole) of the crude product of Example 12b in 30 mL (0.037 mole) of pyridine and the temperature maintained between 5°–10° C. for 2 hr. The mixture was partitioned between water and ether, and the ether layer was washed with 3N hydrochloric acid. The ether layer was washed with brine, charcoaled and dried ($MgSO_4$). The ether was evaporated in vacuo to give 24.1 g (53% yield) of the title compound as a yellow oil.

d.

Octahydro-3-[4-(4-nitrophenoxy)phenyl]-3-indolizinecarbonitrile

A solution of 24.1 g (0.045 mole) of the product of Example 12c in 170 mL of dry DMF was added dropwise to 0.045 mole of sodium hydride (from 2.16 g of 50% sodium hydride washed free of oil with hexane) in 30 ml of dry DMF under argon and stirred at room temperature for 2 hr. The reaction mixture was then poured into water and extracted with ether. The ether layer was washed with brine, dried ($MgSO_4$), and the ether evaporated in vacuo to give 16.7 g of the crude title compound as a brown oil.

e.

1,5,6,7,8,8a-hexahydro-3-[4-(4-nitrophenoxy)]phenyl]-2H-indolizinium Perchlorate A 15 mL (0.17 mole of 70% aqueous perchloric acid was added to 16.7 g of the crude product of Example 12d in 120 mL of ethanol and stirred for 1 hr with heating. The atmosphere over the reaction was flushed with nitrogen into a sodium hypochlorite trap. The solid was collected and recrystallized twice from ethanol to give 11.1 g (56.6% yield) of the title compound.

f.

N-[4-[4-trans-Octahydro-3-indolizinyl)phenoxy]-phenylacetamide

A 7.5 g (0.017 mole) sample of the product of Example 11e was added to a solution of 3.23 mL 90.034 mole) of acetic anhydride in 100 mL of glacial acetic acid and 150 mg of platinum oxide added. The mixture was placed on the Parr apparatus under 50 psi of hydrogen and allowed to run for 9 hr. The hydrogen uptake was 35 psi. The mixture was filtered and the solvent was evaporated in vacuo to give an oil. The oil was partitioned between 10% sodium hydroxide and ether, and the ether layer was washed with brine, dried ($K_2CO_3$), and the ether evaporated in vacuo to an oil. The oil was flash chromatographed in $SiO_2$ using 66% hexane, 33% acetone as the eluant. The major product bearing fractions were pooled, and the solvent was evaporated in vacuo to give an oil which crystallized on standing. The solid was recrystallized from toluene-hexane to give 3.43 g (57.6% yield) of the title compound as white solid, mp=121°-123° C.

EXAMPLE 13 a.

2-(2-Chloroethyl)piperidine Hydrochloride

A 27.2 g (0.2 mole) sample of 2-(2-hydroxyethyl)-piperidine was treated with ethereal hydrogen chloride and the salt was dried briefly. The solid was dissolved in 125 mL of warm chloroform and then 33.5 mL (0.46) of thionyl chloride was added in portions to the solution. The mixture was refluxed for 2.5 hr. The reaction mixture was cooled to room temperature, and the solvent evaporated in vacuo to a brown solid. The solid was recrystallized from ethanol-ether to give 17 g (46% yield) of the title compound as solid, mp=160°-162° C.

b.

2-(2-chloroethyl)-alpha-(2-chloro-4-fluorophenyl)-1-piperidine acetonitrile A 11.6 g (0.073 mole) sample of 2-chloro-4-fluorobenzaldehyde was added to a solution of 13.5 g (0.073 mole) of the product of Example 13a in 100 mL of water and 3.9 g (0.08 mole) of sodium cyanide was added. the mixture was allowed to stir at room temperature for three days. The reaction mixture was extracted with ether, and the ether layer was dried (MgSO4), and the ether evaporated in vacuo to give 25.3 g of the title compound as a yellow oil.

c.

trans-3-(2-chloro-4-fluorophenyl)octahydro-3-indolizinecarbonitrile

A 25.3 g sample of the crude product of Example 13b was dissolved in 150 mL of dry DMF and added in portions to a suspension of 0.073 mole of sodium hydride (from 3.5 g of 50% sodium hydride washed free of oil with hexane) in 25 mL of dry DMF and stirred at room temperature overnight. Water was added, and the mixture was extracted with ether. The ether layer was washed with brine, dried (MgSO4), and the ether was evaporated in vacuo to give 17.8 g of the title compound as an oil.

d.

trans-3-(2-chloro-4-fluorophenyl)octahydroindolizine

A solution of 17.8 g (0.064 mole) of the crude product of Example 13c in 150 mL of ether was added in portions to a suspension of 9.7 g (0.026 mole) of lithium aluminum hydride in 100 mL of anhydrous ether, and the mixture refluxed under a nitrogen atmosphere for 3 hr. The reaction mixture was cooled to room temperature, and the excess lithium aluminum hydride was decomposed with water and sodium hydroxide. The mixture was filtered, and the filtrate was dried (K2CO3). The ether was evaporated in vacuo to an oil residue. The oil was flash chromatographed on SiO2 using 98% hexane, 2% EtOAc as the eluant. The first major product bearing fractions were pooled, and the solvent evaporated in vacuo to give 7.3 g (45% yield) of the title compound as an oil.

e.

N-[3-chloro-4-[[4-(trans-octahydro-3-indolizinyl)-phenyl]thio]phenyl acetamide Hydrochloride A solution of 2.56 g (0.013 mole) of 4-acetamidothiophenyl in 60 mL of dry 1,3-imidazolin-2-one was added in portions to a suspension of 0.013 mole of sodium hydride (from 0.662 g of 50% sodium hydride washed free of oil with hexane) in 5 mL of 1,3-imidazolin-2-one until the NaH had dissolved. Then 3.5 g (0.013 mole) of the product of Example 13d was added and the reaction mixture was refluxed overnight under argon. An additional solution of sodium thiophenolate was prepared separately using the same amounts of 4-acetamidothiophenol and sodium hydride and this solution was added to the original reaction mixture, then the mixture was refluxed overnight. The reaction mixture was cooled, water was added, and the mixture was extracted with ether. The ether layer was washed with brine, dried (K2CO3), and the ether was evaporated in vacuo to an oil. The oil was flash chromatographed on SiO2 using 80% hexane, 20% acetone as the eluant. The first major product bearing fractions were pooled, and the solvent evaporated in vacuo to an oil that crystallized on standing. The solid was recrystallized from EtOAc-methylcyclohexane to give 2.38 g (43% yield) of the title compound as a white solid, mp=157°-159.5° C.

What is claimed is:

1. An octahydroindolizine of the following formula (I):

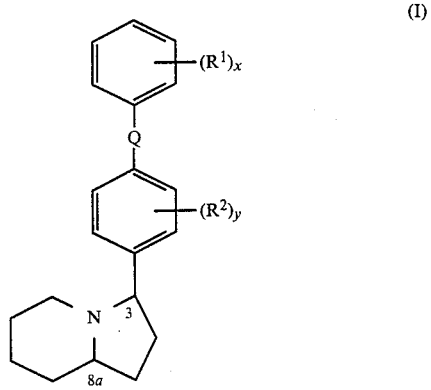

wherein
Q is —NR—, —(CH$_2$)$_z$—, —CH=CH—, —C≡C—, —OCH$_2$—, —SCH$_2$—, —SO$_2$—, —SO—, —CO—, or an oxygen or a sulfur atom;
R is hydrogen or alkyl of about 1 to 4 carbons;
R$^1$ is independently amino, alkylamino of about 1 to 4 carbons, dialkylamino of about 1 to 4 carbons in each alkyl group, —SR$^3$, —SOR$^4$, —SO$_2$R$^5$, —COOR$^6$, —COR$^7$, —NR$^8$COR$^9$, alkyl of about 1 to 4 carbons, alkoxy of about 1 to 4 carbons, haloalkyl of about 1 to 4 carbons, nitro, cyano or halo;
R$^2$ is independently alkyl of about 1 to 4 carbons, alkoxy of about 1 to 4 carbons, halo, haloalkyl of about 1 to 4 carbons, alkylthio of about 1 to 4 carbons or cyano;

$R^3$ is hydrogen or alkyl of about 1 to 4 carbons;

$R^4$ is alkyl of about 1 to 4 carbons;

$R^5$ is alkyl of about 1 to 4 carbons;

$R^6$ is alkyl of about 1 to 4 carbons;

$R^7$ is hydrogen or alkyl of about 1 to 4 carbons;

$R^8$ is hydrogen or alkyl of about 1 to 4 carbons;

$R^9$ is hydrogen or alkyl of about 1 to 4 carbons;

x is the integer 0, 1, 2 or 3;

y is the integer 0, 1, 2 or 3; and z is the integer 0, 1, 2 or 3, and the pharmaceutically-acceptable acid-addition salts thereof.

2. The octahydroindolizine of claim 1, wherein said halo for $R^1$ and $R^2$ and the halo portion of said haloalkyl for $R^1$ and $R^2$ is fluoro, chloro, bromo or iodo.

3. The octahydroindolizine of claim 1, wherein the 3-position substituent and the 8a-position hydrogen of formula (I) are trans to each other.

4. The octahydroindolizine of claim 3, wherein said octahydroindolizine is the (+) isomer.

5. The octahydroindolizine of claim 3, wherein said octahydroindolizine is the (−) isomer.

6. The octahydroindolizine of claim 1, wherein Q represents —(CH$_2$)$_z$—, —CH=CH—, —C≡C—, —OCH$_2$— or an oxygen or a sulfur atom.

7. The octahydroindolizine of claim 6, wherein Q is a sulfur atom.

8. The octahydroindolizine of claim 1, wherein $R^1$ is —NR$^8$COR$^9$.

9. The octahydroindolizine of claim 1, wherein $R^1$ is —NHCOCH$_3$.

10. The octahydroindolizine of claim 1, wherein said octahydroindolizine is selected from the group consisting of:

N-[4-[[4-(octahydro-3-indolizinyl)phenyl]thio]phenyl]acetamide;

N-[3-[[4-(octahydro-3-indolizinyl)phenyl]ethynyl]phenyl]acetamide;

3-[4-(phenylmethoxy)phenyl]octahydroindolizine;

N-[3-[2-[4-(octahydro-3-indolizinyl)phenyl]ethenyl]phenyl]acetamide;

octahydro-3-[4-(phenylethynyl)phenyl]indolizine;

octahydro-3-[4-(2-phenylethyl)phenyl]indolizine;

3-[4-[(4-methylphenyl)thio]phenyl]octahydroindolizine;

3-[4-[(4-chlorophenyl)thio]phenyl]octahydroindolizine;

N-[3-[2-[4-(octahydro-3-indolizinyl)phenyl]ethyl]phenyl]acetamide;

3-[[4-(octahydro-3-indolizinyl)phenyl]thio]benzenamine;

N-[3-[[4-(octahydro-3-indolizinyl)phenyl]thio]phenyl]acetamide;

N-[4-[4-(octahydro-3-indolizinyl)phenoxy]phenyl]acetamide; and

N-[4-[[3-chloro-4-(octahydro-3-indolizinyl)phenyl]thio]phenyl]acetamide.

or a pharmaceutically-acceptable acid-addition salt thereof.

11. The octahydroindolizine of claim 1, which is trans N-[4-[[4-(octahydro-3-indolizinyl)phenyl]thio]phenyl]acetamide or a pharmaceutically-acceptable acid-addition salt thereof.

12. A pharmaceutical composition for alleviation of pain which comprises a pharmaceutically-acceptable carrier in combination with an analgesically effective amount of an octahydroindolizine of claim 1.

13. A method of relieving pain in a mammal which comprises administering to a mammal in need thereof the pharmaceutical composition of claim 12.

14. The method of claim 13, wherein said mammal is a human.

* * * * *